United States Patent [19]
Chang et al.

[11] Patent Number: 5,811,468
[45] Date of Patent: Sep. 22, 1998

[54] COMBINATION GAS DISENGAGING DOWNCOMER-REJUVENATION TUBE FOR IN-SITU SLURRY CATALYST REJUVENATION (LAW541)

[75] Inventors: Min Chang, Warren; Constantine A. Coulaloglou, Mendham; Edward C. Hsu, Bridgewater, all of N.J.

[73] Assignee: Exxon Research and Engineering Company, Florham Park, N.J.

[21] Appl. No.: 851,865

[22] Filed: May 6, 1997

[51] Int. Cl.$^6$ ................................................... C07C 27/00
[52] U.S. Cl. .......................... 518/700; 422/219; 422/230; 422/231; 502/21; 502/22; 502/20; 502/30
[58] Field of Search ............................... 518/700; 502/21, 502/22, 20, 30; 422/230, 231, 219

[56] References Cited

U.S. PATENT DOCUMENTS

| | | |
|---|---|---|
| 5,260,239 | 11/1993 | Hsia ........................................... 502/30 |
| 5,283,216 | 2/1994 | Mitchell ..................................... 502/30 |
| 5,288,673 | 2/1994 | Behrmann et al. ........................ 502/30 |
| 5,382,748 | 1/1995 | Behrmann et al. ...................... 585/899 |

*Primary Examiner*—Gary Geist
*Assistant Examiner*—Jafar Parsa
*Attorney, Agent, or Firm*—Jay Simon

[57] ABSTRACT

A reversibly deactivated, particulate catalyst in a hydrocarbon synthesis slurry is rejuvenated by circulating the slurry from a slurry body through (i) a gas disengaging zone to remove gas bubbles from the slurry and increase its density, (ii) a downcomer which feeds the gas reduced, dense slurry into the bottom of a rejuvenating tube and applies a positive hydrostatic pressure to the tube, (iii) a catalyst rejuvenation zone in which a catalyst rejuvenating gas, which also acts as a lift gas, contacts the catalyst in slurry to form a catalyst rejuvenated slurry and, (iv) back into the slurry body. Removing gas bubbles prior to rejuvenation improves the rejuvenation efficiency and the downcomer reduces the amount of rejuvenation gas required to maintain slurry circulation through the tube.

18 Claims, 2 Drawing Sheets

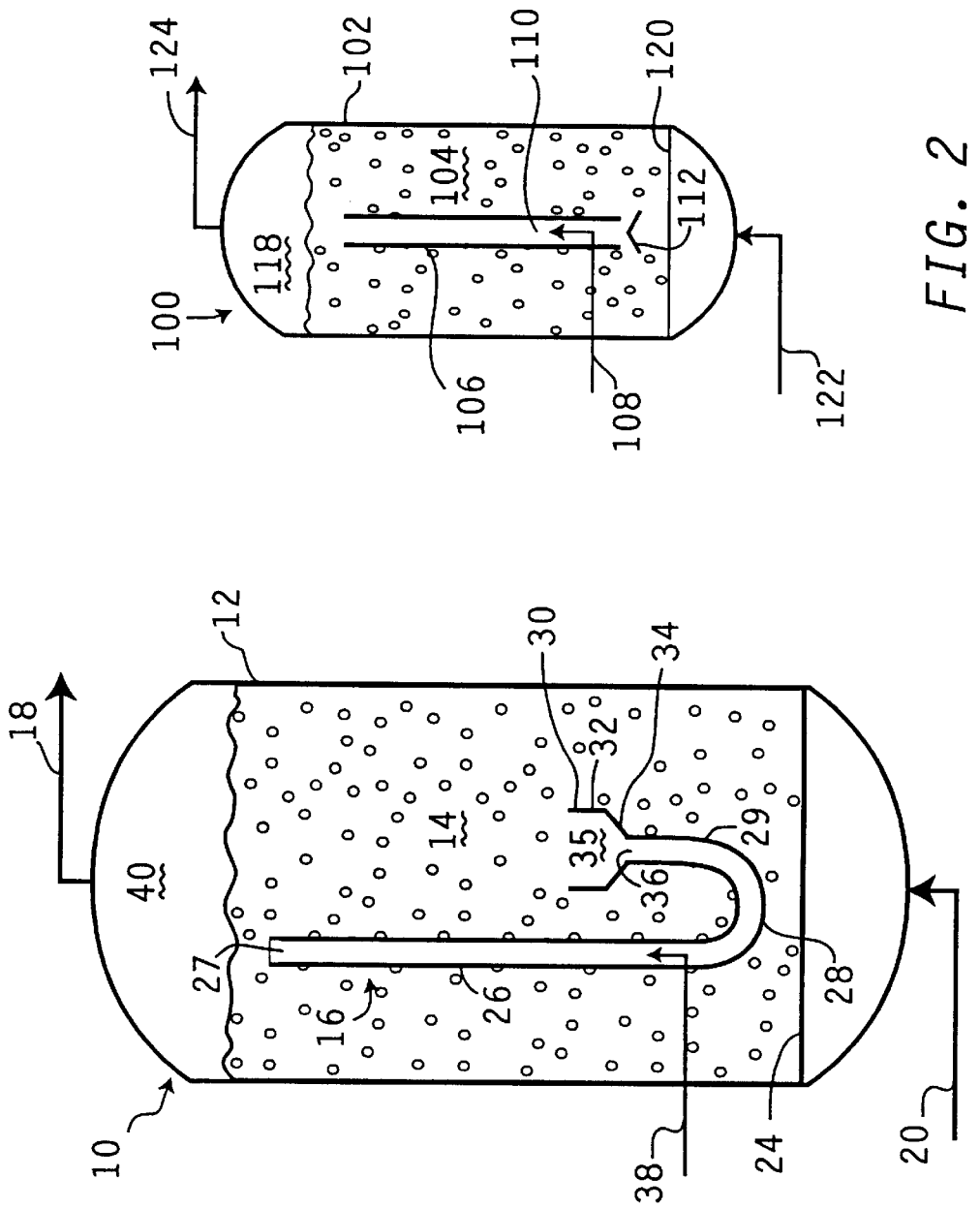

COMBINATION GAS DISENGAGING DOWNCOMER-REJUVENATION TUBE FOR IN-SITU SLURRY CATALYST REJUVENATION (LAW541)

BACKGROUND OF THE DISCLOSURE

1. Field of the Invention

The invention relates to a process and means for rejuvenating catalyst particles in-situ in a slurry. More particularly, the invention relates to a process and means for rejuvenating solid catalyst particles in-situ in a three phase, Fischer-Tropsch type hydrocarbon synthesis slurry comprising said particles and gas bubbles in a hydrocarbon slurry liquid, using a combination gas disengaging downcomer and rejuvenation tube.

2. Background of the Invention

Slurry hydrocarbon synthesis (HCS) processes are known. In a slurry HCS process a synthesis gas (syngas) comprising a mixture of $H_2$ and CO is bubbled up as a third phase through a slurry in a reactor in which the slurry liquid comprises hydrocarbon products of the synthesis reaction and the dispersed, suspended solids comprise a suitable Fischer-Tropsch type hydrocarbon synthesis catalyst. Reactors which contain such a three phase slurry are sometimes referred to as "bubble columns", as is disclosed in U.S. Pat. No. 5,348,982. Irrespective of whether the slurry reactor is operated as a dispersed or slumped bed, the mixing conditions in the slurry will typically be somewhere between the two theoretical conditions of plug flow and back mixed. One or more gas disengaging downcomers may be used in maintaining catalyst distribution as is disclosed in U.S. Pat. No. 5,382,748. Syngas made from hydrocarbon feedstocks which contain nitrogen (i.e., natural gas) or nitrogen containing compounds (i.e., resids, coal, shale, coke, tar sands, etc.) invariably contains HCN and $NH_3$ which contaminate the reactive slurry and rapidly, but reversibly, deactivate the catalyst. Certain oxygenates and carbonaceous compounds formed in the slurry as by-products of the HCS reaction can also cause rapid deactivation. Deactivation of such catalysts by these species is reversible and catalytic activity is restored (the catalyst rejuvenated) by contacting the deactivated catalyst with hydrogen. The activity of the HCS catalyst in the reactive slurry may be intermittently or continuously rejuvenated by contacting the slurry with hydrogen or a hydrogen containing rejuvenation gas to form a rejuvenated catalyst slurry as is disclosed, for example, in U.S. Pat. Nos. 5,260,239 and 5,268,344. In these patents the slurry, containing gas bubbles, is rejuvenated by circulating it through either a rejuvenation tube immersed in the slurry or an external rejuvenation vessel. The rejuvenation gas also acts as a lift gas to circulate slurry through the tube. It has now been found that the presence of CO hinders catalyst rejuvenation until the CO is consumed. This limits the overall efficiency of the rejuvenation process and wastes CO and $H_2$. It would be an improvement to the art if these gas bubbles could be removed from the slurry before it contacts the rejuvenation gas. It would be a still further improvement if the slurry circulation through the tube could be achieved with less rejuvenation gas.

SUMMARY OF THE INVENTION

The invention relates to a process and means for rejuvenating solid catalyst particles in a three phase hydrocarbon synthesis (HCS) slurry comprising gas bubbles and catalyst particles dispersed in a hydrocarbon slurry liquid, in which gas bubbles are removed from the slurry prior to rejuvenation and a downcomer provides a hydrostatic head to the rejuvenation zone to achieve the desired slurry circulation with less lift gas. Briefly, the process comprises passing a portion of slurry, from a slurry body in which at least a portion of the catalyst is reversibly deactivated, through a gas disengaging zone to remove gas bubbles and into a downcomer which feeds the gas reduced slurry into a catalyst rejuvenation zone in which it contacts gas which rejuvenates the catalyst. This may be accomplished by a combination gas disengaging downcomer and rejuvenation tube immersed in the slurry body. The open top of the rejuvenation tube may be outside the slurry body. The catalyst rejuvenation is done either continuously or intermittently, as desired, with the slurry reactor either operating and producing hydrocarbon products, or with it off-line. The gas bubbles comprise valuable unreacted synthesis gas (syngas) which interferes with the catalyst rejuvenation and would otherwise be wasted, along with gas products of the HCS reaction. The slurry liquid comprises hydrocarbon products of the HCS reaction which are liquid at the reaction conditions. The gas injected into the rejuvenation zone rejuvenates the catalyst in the slurry and, at the same time, serves as a lift gas to insure circulation of the slurry through the rejuvenation zone. The gas reduced slurry is denser than that comprising the slurry body and the slurry mixed with rejuvenating lift gas in the rejuvenating zone. This enables the downcomer to apply a hydrostatic pressure to the bottom of the rejuvenation zone which is determined in part by the difference in densities of the gas reduced slurry in the downcomer, the slurry body, the gas filled slurry in the rejuvenation zone, and the vertical distance between the top of the downcomer and the gas injection point in the rejuvenation zone. This means that less lift gas is required to maintain a given slurry circulation rate through the rejuvenation zone. The rejuvenation gas, which also serves as a lift gas, will comprise hydrogen in the case of rejuvenating a slurry HCS catalyst. It may be all hydrogen or hydrogen mixed with one or more other gasses as explained in detail below.

The combination gas disengaging downcomer and rejuvenation zone may simply be a generally "J" shaped, elongated hollow conduit open at both ends, with the lower leg forming the downcomer portion which terminates at its upper end in an open gas disengaging cup immersed, and upwardly opening, in the slurry body. The longer leg of the J comprises the rejuvenation zone and has means for injecting gas into its interior near the bottom, with the open end or top opening into the top of the slurry body in which it is immersed, or at a location out of the slurry. Catalyst rejuvenation is accomplished within the slurry either in the HCS reactor or reaction zone, or in an outboard or separate catalyst rejuvenation zone or reactor, as is disclosed in U.S. Pat. No. 5,260,239. However, in at least one embodiment it is preferred that the catalyst be rejuvenated within the slurry in the reaction zone. When the practice of the invention is performed in the slurry in an HCS reactor or reaction zone, the HCS reaction is not disturbed, as the gas disengaging, downcomer and catalyst rejuvenation zones, while immersed in the slurry, are separate from it. Further, the rejuvenation process produces an offgas which may contain catalyst deactivating species which will recontaminate the slurry body if this gas is passed back into the slurry body. In this case it is preferred to pass the rejuvenated slurry containing the offgas from the rejuvenating zone to a gas disengaging and separating zone to separate and remove the gas from the slurry, before passing the rejuvenated slurry back into the slurry body.

More specifically, the process of the invention comprises continuously or intermittently circulating a portion of slurry in which the catalyst is at least partially deactivated, from a slurry body successively through (i) a gas disengaging zone to remove gas bubbles from the slurry to form a gas reduced slurry, (ii) a downcomer which passes the gas reduced slurry into a catalyst rejuvenation zone, (iii) a catalyst rejuvenation zone in which a catalyst rejuvenating gas contacts the slurry and at east partially rejuvenates the catalyst particles therein to form a rejuvenated catalyst slurry, and (iv) back into the slurry body, wherein the gas reduced slurry in the downcomer is denser than the slurry in both the rejuvenation zone and the slurry body and applies a positive hydrostatic pressure to the bottom of the rejuvenation zone. In a more specific embodiment relating to a slurry HCS process, the process of the invention comprises the steps of:

(a) contacting a syngas comprising a mixture of $H_2$ and CO in the presence of catalyst deactivating species, with a solid particulate hydrocarbon synthesis catalyst in a slurry body comprising said catalyst and gas bubbles in a hydrocarbon slurry liquid, under reaction conditions effective to form hydrocarbons from said syngas, at least a portion of which are liquid at said reaction conditions, and wherein said species present in said syngas reversibly deactivate said catalyst;

(b) passing a portion of said slurry from said slurry body into a gas disengaging zone to separate gas bubbles from said slurry and form a gas reduced slurry having a density greater than that of both said slurry in said slurry body and the rejuvenated catalyst slurry exiting the rejuvenating zone;

(c) passing said gas reduced slurry through a downcomer and into said catalyst rejuvenation zone, wherein said slurry in said downcomer applies a positive hydrostatic pressure to said slurry in said rejuvenation zone;

(d) passing a gas which comprises a catalyst rejuvenating gas into said rejuvenation zone;

(e) contacting said gas reduced slurry in said rejuvenation zone with said rejuvenating gas which at least partially rejuvenates said catalyst particles therein to form a rejuvenated catalyst slurry containing gas bubbles which has a density less that of said gas reduced slurry, said gas also serving as a lift gas to maintain circulation of said slurry through said zone, and (f) removing said rejuvenated slurry from said rejuvenation zone.

The rejuvenated slurry is then passed directly, or indirectly back into a slurry body, which may or may not be the slurry body from which it was withdrawn, before entering the gas disengaging zone. In a further embodiment the rejuvenated catalyst slurry containing gas bubbles, which comprise offgas, is passed from the rejuvenating zone into a gas separating zone in which offgas is removed from the slurry before it is passed back into a slurry body. This is important to prevent contamination or recontamination of the slurry body with the offgas for the case where the offgas contains catalyst deactivating species produced by the rejuvenation. Still further, the deactivated catalyst present in the slurry may be concentrated in the slurry liquid before being passed into the downcomer, by means which can include gas disengagement and which will be described in detail below. The slurry reactor may be operating during rejuvenation or it may be taken off-line and batch rejuvenated. When rejuvenation occurs while the HCS reactor is on-line and producing hydrocarbon liquids, a portion of the liquids are either continuously or intermittently withdrawn from the reactor. These liquids are further processed into useful products. In a still further embodiment the invention includes generating the syngas by partially combusting a suitable hydrocarbon which contains nitrogen or nitrogen containing compounds to form a syngas comprising a mixture of $H_2$ and CO and which also contains nitrogen species (e.g., HCN and $NH_3$) and/or other species which reversibly deactivate a Fischer-Tropsch type of hydrocarbon synthesis catalyst. By reversibly deactivate in the sense of a Fischer-Tropsch type of hydrocarbon synthesis catalyst is meant that the catalyst activity is restored by contacting the catalyst, in the slurry liquid, with hydrogen or a hydrogen containing gas.

BRIEF DESCRIPTION OF THE DRAWINGS

FIG. 1 is a simplified cross sectional schematic drawing illustrating a slurry reactor containing a catalyst rejuvenating apparatus useful in the practice of the invention.

FIG. 2 is a simple schematic of a slurry reactor containing a catalyst rejuvenation tube of the prior art.

DETAILED DESCRIPTION

Figure 3:
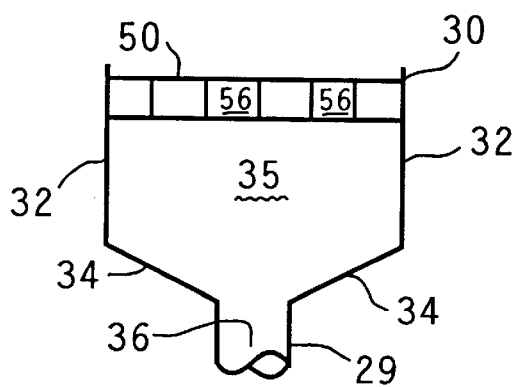
FIG. 3 schematically illustrates a cross section of a slurry degassing cup and downcomer of the invention, in which the cup is provided with a means for reducing turbulence within.

In a Fischer-Tropsch slurry HCS process, a syngas comprising a mixture of $H_2$ and CO is bubbled up into a reactive slurry in which it is catalytically converted into hydrocarbons and preferably liquid hydrocarbons. The mole ratio of the hydrogen to the carbon monoxide may broadly range from about 0.5 to 4, but which is more typically within the range of from about 0.7 to 2.75 and preferably from about 0.7 to 2.5. The stoichiometric mole ratio for a Fischer-Tropsch HCS reaction is 2.0, but there are many reasons for using other than a stoichiometric ratio as those skilled in the art know and a discussion of which is beyond the scope of the present invention. In a slurry HCS process the mole ratio of the $H_2$ to CO is typically about 2.1/1. The syngas may be formed by various means, including contacting a hot carbonaceous material such as coke or coal, with steam, or from a feed comprising methane. A feed comprising methane is preferred for convenience, cleanliness and because it doesn't leave large quantities of ash to be handled and disposed of The methane containing gas feed is fed into a syngas generator and is obtained from natural gas or by burning coal, tar, liquid hydrocarbons and the like. The production of syngas from methane by either partial oxidation, steam reforming or a combination thereof is well known as is disclosed, for example, in U.S. Pat. No. 4,888,131. In many cases it is preferred to catalytically partially oxidize and steam reform the methane in a fluid bed syngas generating unit (FBSG) as is disclosed, for example, in U.S. Pat. Nos. 4,888,131 and 5,160,456. Irrespective of the source of the methane, nitrogen or nitrogen containing compounds are present in the methane containing gas fed into the syngas generator, some of which are converted into $NH_3$ and HCN during the syngas formation. These will deactivate a Fischer-Tropsch HCS catalyst, particularly those comprising Co as the catalytic metal. It has been found that deactivation by these species is reversible and the catalyst can be rejuvenated (the catalytic activity restored) by contacting it with hydrogen. This restoration of the catalytic activity of a reversibly deactivated catalyst is referred to as catalyst rejuvenation. However, while preferred and possible, complete restoration of the catalytic activity for all of the catalyst particles in the slurry passing through the rejuvenation tube may not always be achieved in the process of the invention. It's for this reason the expression "at least partially rejuvenates the catalyst particles therein" and the like, are used herein.

The presence of CO in the rejuvenation zone hinders catalyst rejuvenation until the CO is consumed. Thus, removing at least a portion of the gas bubbles which contain unreacted syngas from the slurry before it is passed into the rejuvenation zone, substantially reduces the amount of CO present in the rejuvenation zone. This reduces the amount of hydrogen needed for the rejuvenation and results in a greater degree of rejuvenation. Further, due to the injection of the hydrogen or hydrogen containing rejuvenation-lift gas into the rejuvenation zone, the $H_2$ to CO ratio in the rejuvenation zone is greater than the stoichiometric 2.1/1 and may be higher than 10/1. This means that instead of being converted to more desirable liquid hydrocarbon products, the CO in the rejuvenation zone is converted primarily to methane, thereby wasting valuable syngas and some of the added hydrogen rejuvenating gas. These gas bubbles also contain gas reaction products of the HCS reaction, of which 50% or more may be water vapor, which interferes with the catalyst rejuvenation by acting as a diluent for the rejuvenation gas. For these reasons it is beneficial to remove as much of the gas bubbles as is possible from the slurry before it is rejuvenated. Further, in the rejuvenation zone the rejuvenation gas also acts as a lift gas to maintain slurry circulation through the zone. Maintenance of slurry circulation requires more gas than is needed strictly for rejuvenation. That is, the total amount of lift gas required to maintain slurry circulation through the rejuvenation tube is more than the amount of hydrogen required to rejuvenate the catalyst particles. In the case of a rejuvenation gas comprising primarily hydrogen, this can mean wasting expensive hydrogen if it can't be separated from the rejuvenation offgas. If the hydrogen (or other rejuvenating gas) gas concentration in the rejuvenation gas is too low, rejuvenation is either incomplete, or inefficient due to the dilution effect from the presence of gas which does not rejuvenate the catalyst, although the lift effect may be more than sufficient. The process and means of the invention is a solution to this dilemma in feeding the degassed slurry into the rejuvenation zone through a downcomer to apply a positive hydrostatic pressure to the slurry in the rejuvenation zone which is independent of the lift gas effect. This results in a substantial reduction in the amount of gas needed to be injected into the rejuvenation zone to maintain the desired slurry circulation.

Referring to FIG. 1 there is schematically illustrated a simplified cross section of a slurry type HCS reactor 10 which comprises a cylindrical reactor vessel 12 containing a three phase slurry 14 and a hollow combination gas disengaging downcomer and catalyst rejuvenating tube 16 of the invention, disposed entirely in the slurry 14. A gas outlet 18 removes product gas, unreacted synthesis gas and gaseous by-products of the catalyst rejuvenation process from the reactor. A syngas feed inlet 20 provides syngas to be admitted into the reactor and injected into the bottom of the slurry by suitable means horizontally disposed across the surface of an otherwise gas and liquid impervious tray 24, as is well known to those skilled in the art. Means for withdrawing the liquid hydrocarbon products from the hydrocarbon synthesis reaction are not shown. The three phase slurry comprises hydrocarbon liquids in which is dispersed bubbles of gas comprising syngas and gas products of the HCS reactions as indicated by small circles, and a solid, particulate catalyst (not shown) for forming hydrocarbon liquids and gasses from the syngas feed. The hydrocarbon slurry liquid comprises hydrocarbon synthesis reaction products which are liquid at the synthesis reaction conditions. Not shown is filtration means, such as one or more liquid filters in the reactive slurry 14 or in one or more filtration vessels external of the reactor. Such filtration means separate the hydrocarbon slurry liquid from the catalyst particles as filtrate, and pass the filtrate to further processing and upgrading. Magnetic means may also be used to separate the catalyst particles from the hydrocarbon liquid product if the catalyst particles are magnetic or paramagnetic, as is disclosed in the prior art. Filtration means is not shown in any of the other Figures for the sake of convenience and simplicity. Inside the reactor, the gas disengaging downcomer and catalyst rejuvenating means 16 of this embodiment includes a substantially vertical, hollow conduit 26 open at its top 27, extending laterally and turning upward at its bottom 28 to form a substantially upward extending, vertical, and hollow downcomer conduit 29, laterally spaced apart from conduit 26 and opening at its top 36 into a vertically extending and upward opening means or cup 30, for disengaging gas bubbles from the slurry and, optionally, also for concentrating catalyst particles in the slurry liquid flowing down therefrom into conduit opening 36. Means 30 comprises a vertical outer wall 32 and a downwardly sloping bottom 34 which define an interior gas disengaging and catalyst concentrating zone 35. The angle of the sloping bottom 34 is greater than the angle of internal friction of the catalyst particles, so that disengaged catalyst particles don't build up on the bottom of means 30. In this embodiment, means 30 has a square horizontal cross-section, although it could also be cylindrical, rectilinear, curvilinear or polygonal. Bottom 34 slopes radially down from outer wall 32 to aperture or opening 36 at its bottom, from which downwardly extending downcomer 29 depends. In the embodiment illustrated in FIGS. 1 and 3, the gas disengaging cup resembles a funnel having a vertically upward extending outer wall or a bucket with a sloping bottom. Other geometries may be used at the convenience and discretion of the practitioner. The essential feature of means 30 include the gas disengaging and catalyst concentrating zone 35, which serves as the downcomer entrance and prevents the upwardly rising gas bubbles in the surrounding slurry body from entering up into the slurry in 35, thereby permitting the gas disengagement. It is also sized so as to provide enough residence time for the slurry flowing down therethrough to achieve a more quiescent, preferably laminar downward flow, to permit maximum coalescence and release of gas bubbles before it enters opening 36 and flows down through the downcomer 29 and up into the vertical rejuvenating zone 26. It may also be sized to permit suspended catalyst particles to drop out of the slurry in and above the cup and concentrate in the slurry liquid entering the rejuvenator through opening 36, which is significantly smaller than the slurry entrance 39 of the disengagement means. That is, the horizontal cross section of the gas disengaging cup is significantly larger than that of the downcomer orifice at the bottom of disengaging zone 35, to provide a slurry residence time sufficient to release gas bubbles and, in a further embodiment, to also achieve a greater net concentration of catalyst in the downcomer than in slurry body 14. The increased catalyst concentration in the gas lean slurry formed in 30 is due in part to the release of the gas bubbles, which results in the slurry passing down through orifice 36 being significantly denser than the slurry in slurry body 14 which contains more gas bubbles. Further, while there is considerable turbulence in the slurry bed 14, slurry just above zone 35, but not in the cup, will also drop catalyst due to a decreased amount of uprising gas bubbles, which serve to keep the catalyst particles in suspension, present immediately above the zone. The turbulence also serves to continuously replace the slurry above the cup. Therefore, if properly sized, the net influx of catalyst into the cup or zone 35 is greater on a proportional basis than the net influx of slurry into zone 35 and out, down through the downcomer 29 and into the rejuvenating zone. Rejuvenating gas comprising hydrogen is passed via line 38 into the interior of vertical conduit 26 which is the catalyst rejuvenating zone, in which the rejuvenating gas contacts the catalyst particles in the gas reduced slurry to rejuvenating gas also acts as a lift gas to lift the slurry containing the rejuvenated catalyst up and out of the top opening 27 and back into the reactive slurry body 14, where the rejuvenated catalyst mixes with the slurry. The gas products of the catalyst rejuvenation reactions, along with unreacted syngas and gas products of the HCS reactions, pass upward and out of the rejuvenator and slurry to gas collection zone 40 and are removed from the reactor via line 18.

The amount of gas in slurry body 14 can range anywhere from about 25–80 volume %. This is present as gas bubbles, with a small amount, i.e., <2% dissolved in the slurry liquid. In one illustration in which the slurry contains 60% gas, a three inch diameter downcomer having a two foot diameter gas disengaging cup at its top, produces a slurry with 30% gas going down the downcomer. This represents 50% gas removal. However, by proper sizing, up to 90% or more can be removed. In another example, a three inch downcomer with a substantially larger gas disengaging cup at its entrance produced a slurry going down through the downcomer having about 10% gas from a 60% gas slurry. This represents a gas removal of almost 85%. The positive hydrostatic pressure applied by the downcomer to the bottom of the rejuvenation zone depends, among other things, on the vertical distance between the top of the downcomer which is above the gas injecting point, and the gas injecting point in the rejuvenation tube. Using a prior art rejuvenation tube (as illustrated in FIG. 2) which was a three inch diameter straight pipe immersed in a slurry having 60% gas, gas flow rates of 2, 3 and 3½ feet per second injected into the tube produced upward slurry flow rates of 0, 0.2 and 0.3 feet per second. In contrast, employing a combination gas disengaging downcomer and rejuvenation tube according to the practice of the invention, as illustrated in FIG. 1 having a fifteen inch diameter and three foot long gas disengaging cup in which the downcomer entrance was about ten feet higher than the gas injection point into the rejuvenation tube, produced slurry flow rates of 1½, 2½ and 3 feet per second at the same gas injection velocities. This demonstrates the operation and efficacy of the invention.

In contrast to the invention, FIG. 2 schematically illustrates a slurry type hydrocarbon synthesis reactor containing a catalyst rejuvenating tube of the prior art. Thus, reactor 100 comprises a cylindrical shell 102 containing a three phase hydrocarbon synthesis slurry 104 and a hollow, vertical catalyst rejuvenating tube 106 within. Gas line 108 injects catalyst rejuvenating gas into the interior 110 of the rejuvenating tube. Slurry flows into the bottom and up the rejuvenating tube where it contacts the rejuvenating gas which rejuvenates the catalyst and sends the rejuvenated catalyst slurry out the top and back into the slurry body 104. The rejuvenating gas also acts as a lift gas to maintain a constant flow of slurry circulating through the rejuvenating tube. Baffle 112 prevents the uprising syntheses gas from entering into the rejuvenating zone 110. The syngas is injected into the bottom of the reactor via line 122 and suitable gas injecting means arrayed across the surface of otherwise gas and liquid impermeable plate 120. The gas rising out of the slurry passes up into gas collecting zone 118 and is removed from the reactor via line 124. In this prior art process, there is no gas disengaging downcomer to disengage gas bubbles and density the slurry before in enters into and up the catalyst rejuvenating tube. The prior art also does not teach providing a positive hydrostatic pressure to the bottom of the tube. Therefore, in the prior art process part of the rejuvenating gas is used to consume the CO present before rejuvenation begins and more gas needs to be injected to maintain slurry circulation up the tube, than with the process and means of the invention.

Figure 4A:
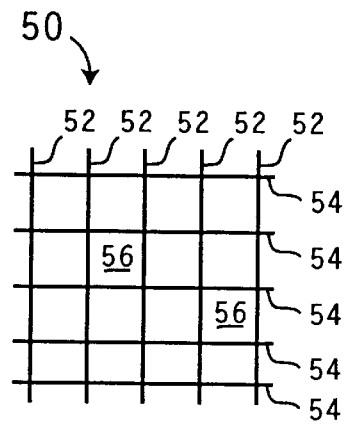
FIGS. 4(a) and 4(b) respectively schematically illustrate a slurry turbulence reducing means shown in FIG. 3, which is fabricated of flat metal strips.
Figure 4B:
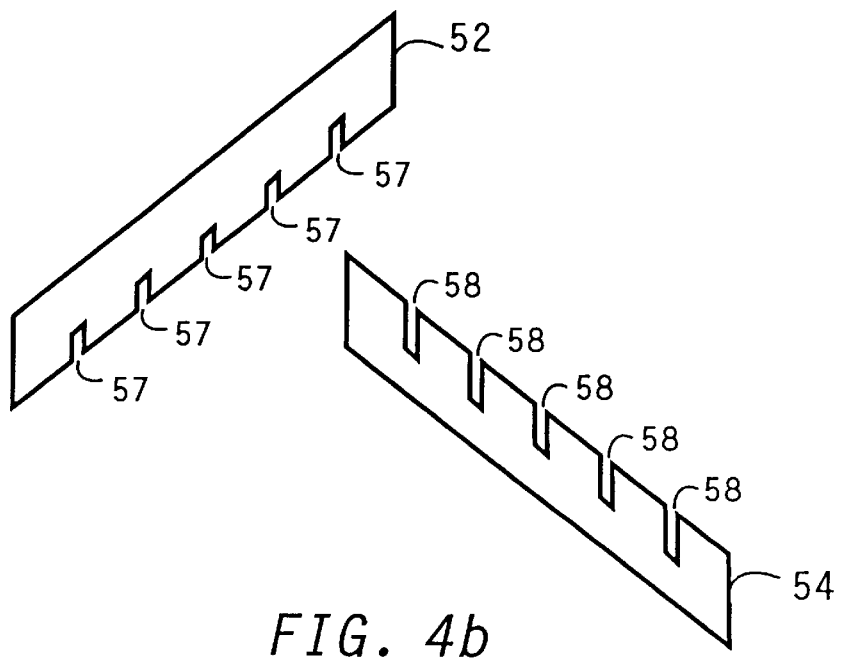

FIG. 3 schematically illustrates a simple cross section of a gas disengaging cup and part of the downcomer downwardly depending therefrom of the invention, in which the gas disengaging means 30 contains means 50 for preventing the turbulence in the main body of slurry in the reactor from disturbing the quiescent slurry in the quiescent flow and disengaging zone 35. One such means, illustrated in FIGS. 3 and 4, comprises a grid or grating made of two sets of flat, parallel and intersecting metal strips, 52 and 54, oriented at right angles to each other and positioned in the top of cup 32 to define a plurality of downwardly oriented conduits 56 of which only two are labeled for convenience, for permitting slurry to flow down into the cup, but which also act as baffles to minimize slurry turbulence outside zone 35 from entering into it and reducing the effectiveness of zone 35 for disengaging both gas bubbles and catalyst particles therein. The strips in each series 54 and 55 are laterally spaced apart from each other and may be fabricated and arranged to intersect in a manner similar to partitions in a box of wine, to create the plurality of vertically orientated, open cells 56. FIG. 4(*b*) schematically illustrates one embodiment of one each of flat strips 52 and 54 having respective laterally spaced apart and parallel grooves 57 and 58 extending halfway up and halfway down the respective strips for fitting into each other in mating engagement to form the turbulence reducing means 50. Two or more sets of means 50 may be positioned in zone 35, vertically spaced apart from each other therein, and the strips may be disposed at an angle other than vertical. Other means may be employed to achieve the same purpose. A means similar to 50 (not shown) may be employed at downcomer entrance 36 to prevent vortex formation.

The hydrogen or hydrogen containing catalyst rejuvenation gas injected into the rejuvenation zone comprises hydrogen which may contain other gasses such as nitrogen, $CO_2$, $H_2O$, $CH_4$, $C_2-C_{4+}$ hydrocarbons, and also CO, as long as the mole ratio of the $H_2$ to CO is sufficient to remove the CO and still rejuvenate at least a portion of the catalyst.

As disclosed in U.S. Pat. No. 5,288,673, the degree of catalyst rejuvenation can be controlled by independently controlling the slurry temperature in the rejuvenating zone irrespective of the temperature of the main body of slurry in the surrounding HCS reaction zone. This patent discloses that temperature control in the rejuvenation zone or tubes is achieved by one or more of either increasing or decreasing the slurry residence time in the zone, so as to utilize the exothermic nature of the rejuvenation reactions, by insulating the rejuvenation tubes, by introducing heat or a cooling medium into the zone, by preheating the rejuvenating gas, etc. The '673 patent teaches that the temperature in the rejuvenation zone should be high enough to remove CO and at least partially rejuvenate the catalyst and low enough to minimize methane formation and wax (~$C_{20}+$ alkanes) hydrogenolysis. These teachings apply to the present invention also.

In an HCS process, liquid and gaseous hydrocarbon products are formed by contacting a syngas comprising a mixture of $H_2$ and CO with a suitable Fischer-Tropsch type of catalyst, under shifting or non-shifting conditions and preferably non-shifting conditions in which little or no water gas shift reaction occurs, particularly when the catalytic metal comprises Co, Ru or mixture thereof Suitable Fischer-Tropsch reaction types of catalyst comprise, for example, one or more Group VIII catalytic metals such as Fe, Ni, Co, Ru and Re. In one embodiment the catalyst comprises catalytically effective amounts of Co and one or more of Re, Ru, Fe, Ni, Th, Zr, Hf, U, Mg and La on a suitable inorganic support material, preferably one which comprises one or more refractory metal oxides. Preferred supports for Co containing catalysts comprise titania, particularly when employing a slurry HCS process in which higher molecular weight, primarily paraffinic liquid hydrocarbon products are desired. Useful catalysts and their preparation are known and illustrative, but nonlimiting examples may be found, for example, in U.S. Pat. Nos. 4,568,663; 4,663,305; 4,542,122; 4,621,072 and 5,545,674.

The hydrocarbons produced by an HCS process according to the invention are typically upgraded to more valuable products, by subjecting all or a portion of the $C_{5+}$ hydrocarbons to fractionation and/or conversion. By conversion is meant one or more operations in which the molecular structure of at least a portion of the hydrocarbon is changed and includes both noncatalytic processing (e.g., steam cracking), and catalytic processing (e.g., catalytic cracking) in which a fraction is contacted with a suitable catalyst. If hydrogen is present as a reactant, such process steps are typically referred to as hydroconversion and include, for example, hydroisomerization, hydrocracking, hydrodewaxing, hydrorefining and the more severe hydrorefining referred to as hydrotreating, all conducted at conditions well known in the literature for hydroconversion of hydrocarbon feeds, including hydrocarbon feeds rich in paraffins. Illustrative, but nonlimiting examples of more valuable products formed by conversion include one or more of a synthetic crude oil, liquid fuel, olefins, solvents, lubricating, industrial or medicinal oil, waxy hydrocarbons, nitrogen and oxygen containing compounds, and the like. Liquid fuel includes one or more of motor gasoline, diesel fuel, jet fuel, and kerosene, while lubricating oil includes, for example, automotive, jet, turbine and metal working oils. Industrial oil includes well drilling fluids, agricultural oils, heat transfer fluids and the like.

It is understood that various other embodiments and modifications in the practice of the invention will be apparent to, and can be readily made by, those skilled in the art without departing from the scope and spirit of the invention described above. Accordingly, it is not intended that the scope of the claims appended hereto be limited to the exact description set forth above, but rather that the claims be construed as encompassing all of the features of patentable novelty which reside in the present invention, including all the features and embodiments which would be treated as equivalents thereof by those skilled in the art to which the invention pertains.

What is claimed is:

1. A vessel containing a three phase slurry and means for contacting a particulate solid dispersed in said slurry with a gas, said slurry comprising said particulate solid, gas bubbles and a slurry liquid, said means comprising a gas disengaging downcomer in internal fluid communication with a hollow conduit containing gas injecting means for injecting gas into its interior, wherein the top of said downcomer is vertically higher than the gas injecting position of said conduit, whereby fluid flowing down the downcomer exerts a positive hydrostatic pressure to the interior bottom of said conduit.

2. A vessel according to claim 1 wherein said slurry comprises a particulate hydrocarbon synthesis catalyst, said gas bubbles comprise syngas and said liquid comprises hydrocarbon products hydrocarbon synthesis reaction between said gas and catalyst.

3. A vessel according to claim 2 comprising a hydrocarbon synthesis reactor.

4. A vessel according to claim 3 wherein said means comprises an elongate, hollow, unitary conduit comprising a downcomer portion and a catalyst rejuvenation portion with said gas disengaging means located proximate the top of said downcomer portion and wherein said downcomer portion is shorter than said rejuvenation portion and its top is lower than the top of said rejuvenate portion.

5. A slurry hydrocarbon synthesis process for producing hydrocarbons comprising:

(a) contacting a synthesis gas comprising a mixture of $H_2$ and CO in the presence of catalyst deactivating species, with a solid particulate hydrocarbon synthesis catalyst in a slurry body comprising said catalyst and gas bubbles in a hydrocarbon slurry liquid, under reaction conditions effective to form hydrocarbons from said synthesis gas, at least a portion of which are liquid at said reaction conditions, and wherein said species present in said synthesis gas reversibly deactivate said catalyst;

(b) passing a portion of said slurry from said slurry body into a gas disengaging zone to separate gas bubbles from said slurry and form a gas reduced slurry having a density greater than that of both said slurry in said slurry body and the rejuvenated catalyst slurry exiting the rejuvenating zone;

(c) passing said gas reduced slurry through a downcomer and into said catalyst rejuvenation zone, wherein said slurry in said downcomer applies a positive hydrostatic pressure to said slurry in said rejuvenation zone;

(d) passing a gas which comprises a catalyst rejuvenating gas into said rejuvenation zone;

(e) contacting said gas reduced slurry in said rejuvenation zone with said rejuvenation gas which at least partially rejuvenates said catalyst particles therein to form a rejuvenated catalyst slurry containing gas bubbles which has a density less that of said gas reduced slurry, said gas also serving as a lift gas to maintain circulation of said slurry through said zone, and (f) removing said rejuvenated slurry from said rejuvenation zone.

6. A process according to claim 5 wherein said rejuvenated slurry is passed back into said slurry body.

7. A process according to claim 6 wherein said catalyst comprises at least one supported Group VIII metal.

8. A process according to claim 6 wherein said gas bubbles are removed from said rejuvenated slurry before it is passed back into said slurry body.

9. A process according to claim 8 wherein said catalyst contains cobalt.

10. A process according to claim 7 wherein at least a portion of said synthesized hydrocarbons are upgraded by conversion by a non-catalytic process.

11. A process according to claim 10 wherein the non-catalytic process is steam cracking.

12. A process according to claim 7 wherein at least a portion of said synthesized hydrocarbons are upgraded by conversion by a catalytic process.

13. A process according to claim 12 wherein the process is fluid catalytic cracking.

14. A process according to claim 12 wherein the process is conducted in the presence of hydrogen.

15. A process according to claim 14 wherein the process is hydroconversion.

16. A process in accordance with claim 15 wherein the process is hydroisomerization.

17. A process in accordance with claim 15 wherein the process is hydrodewaxing.

18. A process in accordance with claim 15 wherein a fuel selected from the group consisting of jet fuel and diesel fuel is recovered.

* * * * *